US008282050B2

(12) United States Patent
Georgey (10) Patent No.: US 8,282,050 B2
(45) Date of Patent: Oct. 9, 2012

(54) HOSE SUPPORT DEVICE FOR CPAP MACHINE

(76) Inventor: Yorgi Georgey, Toronto (CA)

( * ) Notice: Subject to any disclaimer, the term of this patent is extended or adjusted under 35 U.S.C. 154(b) by 513 days.

(21) Appl. No.: 12/543,642

(22) Filed: Aug. 19, 2009

(65) Prior Publication Data

US 2010/0294897 A1 Nov. 25, 2010

(30) Foreign Application Priority Data

May 20, 2009 (CA) .................................. 2666218

(51) Int. Cl.
*B65H 75/48* (2006.01)
(52) U.S. Cl. ........................... 248/79; 248/80; 248/349.1
(58) Field of Classification Search .............. 248/349.1, 248/79, 75, 80, 89, 90; 242/370, 398
See application file for complete search history.

(56) References Cited

U.S. PATENT DOCUMENTS

| | | | |
|---|---|---|---|
| 4,373,523 A | | 2/1983 | Treutelaar |
| 5,390,695 A | * | 2/1995 | Howard .................... 137/355.27 |
| 5,490,805 A | | 2/1996 | Bredesen |
| 5,697,572 A | * | 12/1997 | Salentine et al. ............. 242/379 |
| 5,902,164 A | | 5/1999 | Shoemaker |
| 6,290,158 B1 | | 9/2001 | Huang |
| 6,766,588 B1 | * | 7/2004 | Hsu .................................. 33/755 |
| 6,929,209 B2 | * | 8/2005 | Baumgarten ................. 242/377 |
| 6,994,289 B2 | | 2/2006 | Liao |
| 7,040,581 B2 | | 5/2006 | Noelke et al. |
| 7,857,000 B1 | * | 12/2010 | Langdon .................. 137/355.27 |
| 2009/0166462 A1 | * | 7/2009 | Chang ........................... 242/375 |
| 2012/0025002 A1 | * | 2/2012 | Zink .......................... 242/390.2 |

* cited by examiner

*Primary Examiner* — Terrell McKinnon
*Assistant Examiner* — Steven Marsh
(74) *Attorney, Agent, or Firm* — McMillan LLP (57) ABSTRACT

The invention comprises a hose support for supporting a hose extending from a CPAP or oxygen machine to a mask on a user. The hose support comprises a housing, a reel mounted within said housing and having a tape wound thereon, a tensioning mechanism operatively connected to said tape for maintaining a pre-determined tension in said tape, such that the tape extends when under a tension greater than said pre-determined tension and retracts when slack is provided, and a connector attached to a free end of said tape, said connector sized and dimensioned to be secured to a fixed position on the hose. The fixed position defining a tensioned segment of the hose, extending from said connector to the mask. The pre-determined tension is selected to support the tensioned segment of the hose away from the user, and wherein said tape extends and retracts in response to movement of the user, thereby maintaining the tensioned segment away from the user. Preferably, the pre-determined tensioned is adjustable such that the hose support is adaptable to different CPAP machines and mounting arrangements.

16 Claims, 10 Drawing Sheets

HOSE SUPPORT DEVICE FOR CPAP MACHINE

FIELD OF THE INVENTION

The present invention relates to the field of oxygen mask and hose support devices and in particular to a hose support, and preferably an adjustable tension hose support, for use with a CPAP, or oxygen machine which maintains a portion of the hose away from the user while imparting an insignificant force on the mask.

BACKGROUND OF THE INVENTION

Sleep apnea is a sleep disorder affecting millions of individuals worldwide. A common treatment for sleep apnea is the use of a CPAP (Continuous Positive Airway Pressure) machine to force compressed air into the sleeper's airway during sleep to prevent obstruction (sleep apnea). The sleeper wears an air breathing mask and receives the compressed air through an air hose connected to a compressor which is typically located on the floor or on a table near the sleeper's bed.

While the use of a CPAP machine has been demonstrated to be effective in addressing sleep apnea, the device is not without drawbacks. One such drawback arises from the use of an air hose and mask with a non-restrained sleeper. As the sleeper moves during the night, the mask and hose are required to move as well. This can lead to tangling of the hose, and to force being exerted upon the mask. As a result, the mask can become dislodged or even detached, defeating the purpose of the CPAP machine.

U.S. Pat. No. 7,040,581 to Noelke et al., issued May 9, 2006, discloses a cantilever structure for supporting an oxygen hose above a patient's head. A bi-pod style support pole is secured to the bed or mattress and a pulley and cantilever arm is used to support the hose. The arm pivots to allow for movement of the hose in response to patient movement and the pulley is spring-loaded to absorb any resulting vibration and shock. The Noelke device exerts a pulling tension upon the hose at all times, which can be translated into a pulling tension on the patient's breathing mask, leading to discomfort or even to dislodging of the mask.

U.S. Pat. No. 4,373,523 to Treutelaar, issued Feb. 15, 1983, discloses a helmet for use with patients in traction. The helmet has a pair of extension projecting from the front of the patient's face which support a constant tension (spring-loaded) reel. The reel cable is then attached to the esophageal tube and/or other tubes required by the patient at a point between the reel and the patient's mouth. The helmet and reel device permits the patient to move their head without the risk of dislodging the tubes from their body. The Treutelaar device is designed for use with a patient with minimal movement, and the helmet design would not be suitable for an active, mobile sleeper.

Thus, there is a need for a support for a CPAP machine air hose that prevents the hose from becoming tangled during sleeping while also exerting minimal force upon the breathing mask.

It is an object of this invention to partially or completely fulfill one or more of the above-mentioned needs.

SUMMARY OF THE INVENTION

According to one embodiment of the present invention, a hose support for supporting a hose extending from a CPAP machine to a mask on a user is disclosed. Preferably, the hose support comprises a tension adjustment mechanism. The hose support comprises a housing, a reel mounted within said housing and having a tape wound thereon, a tensioning mechanism operatively connected to said tape for maintaining a pre-determined tension in said tape, such that the tape extends when under a tension greater than said pre-determined tension and retracts when slack is provided, a connector attached to a free end of said tape, said connector sized and dimensioned to be secured to a fixed position on the hose; said fixed position defining a tensioned segment of the hose, extending from said connector to the mask, wherein said pre-determined tension is selected by the user to support the tensioned segment of the hose away from the user, and wherein said tape extends and retracts in response to movement of the user, thereby maintaining the tensioned segment away from the user.

Preferably, the said tensioning mechanism comprises a constant force spring having a fixed end operatively connected within said reel.

The tension adjusting mechanism is preferably a selectively rotatable post operatively connected to said extendable end of said constant force spring for applying an initial tension to said constant force spring. On the interior or exterior of the housing, the selectively rotatable post is operatively connected to a knob for rotating the post, thereby applying the initial tension to the constant force spring. One or more gears may be operatively connected to the knob and or to the rotatable post to produce a desired ratio of knob rotations to post rotations.

Two or more rollers can be positioned at an exit of said housing to orient the tape with respect to the reel.

Preferably, the housing is mounted vertically higher than the user by a mounting device which may include a ceiling mount with a hook, or a base attached to a wall mount, a headboard mount, a mattress mount, a bed frame mount or a floor mount. Alternatively, a base having an extendable pole and a hook may be provided to mount the hose support without requiring installation on a wall or ceiling. Such a base can be on a wheel support for portability and further collapsible into a size and dimension similar to the CPAP machine for storage and transport.

Other and further advantages and features of the invention will be apparent to those skilled in the art from the following detailed description thereof, taken in conjunction with the accompanying drawings.

BRIEF DESCRIPTION OF THE DRAWINGS

The invention will now be described in more detail, by way of example only, with reference to the accompanying drawings, in which like numbers refer to like elements, wherein.

DETAILED DESCRIPTION OF THE PREFERRED EMBODIMENTS

The inventive device presented herein comprises a hose support 100, and preferably an adjustable tension hose support, which is secured to a mount and used to support an air hose for a CPAP machine while the user is sleeping.

Figure 1:
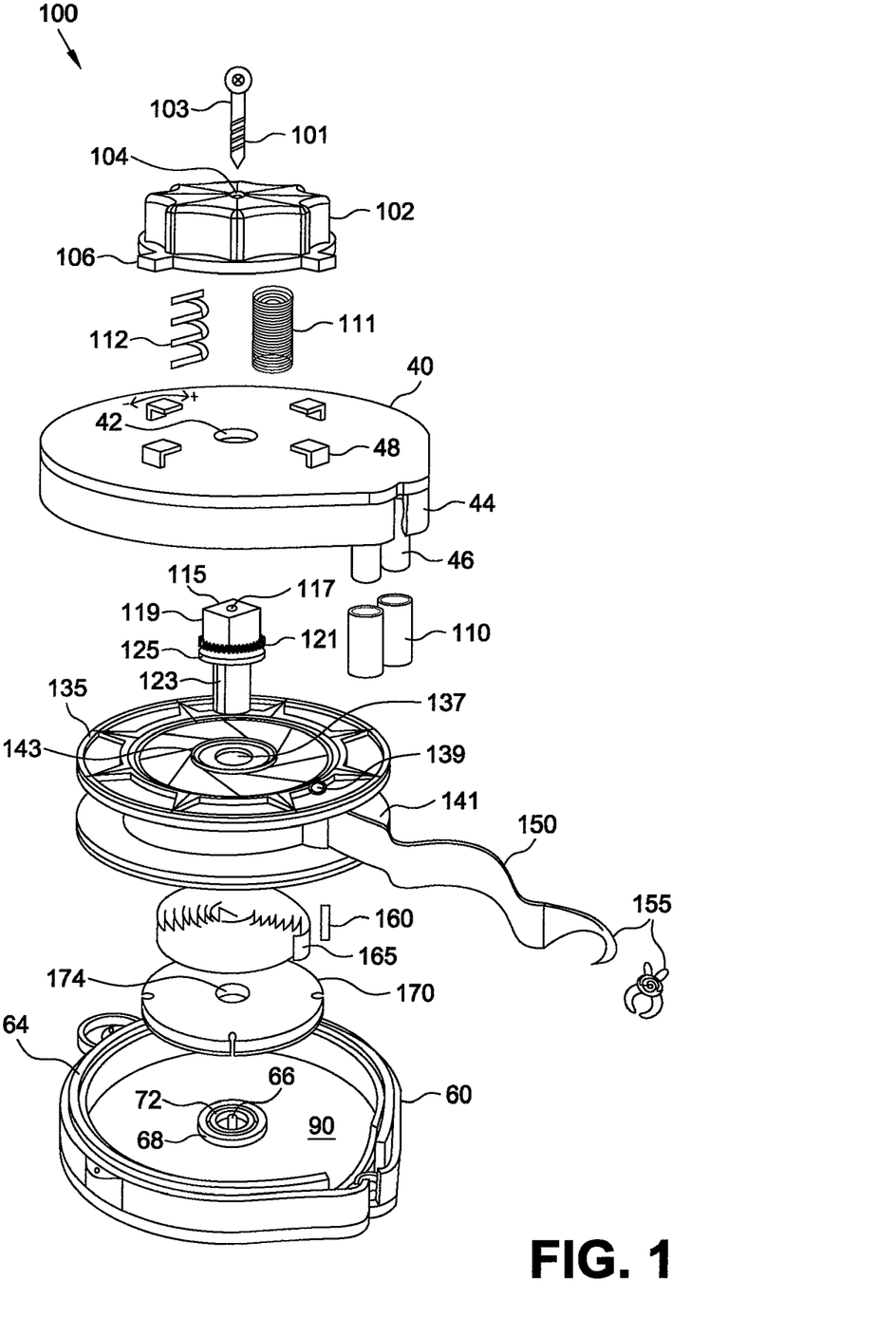
FIG. 1 is an exploded perspective view taken from the top of the hose support device according to one embodiment of the present invention.

The adjustable tension hose support 100, as shown in FIG. 1, comprises a housing 90, preferably formed from two portions 40 and 60. Inside the housing 90, a reel 135 is provided having a tape 150 retractably mounted thereon. The tape 150 is operatively connected to a tensioning mechanism, preferably constant force spring 165, for maintaining a pre-determined tension in the tape 150 such that the tape 150 extends when under a tension greater than the pre-determined tension and retracts when slack is provided. Tape 150 may alternatively be a cable, a rope, or any other cord means which can be wound onto reel 135.

The free end of the tape 150 passes through opening 44 to the exterior of the housing 90 and has a connector attached thereto. As shown in the Figures, the connector comprises a clip 155 and is sized and dimensioned to be secured to a fixed position on the hose (not shown). At the fixed position, i.e. at the clip 155, the hose is functionally divided into a tensioned segment extending from the clip 155 to a mask on the user and a slacked segment extending from the CPAP machine (not shown) to the clip 155. Alternatively the connector could be a clip, a Velcro™ strap or any other connecting means to which a hose can be connected. The pre-determined tension is selected such that, as will be further described below, the tensioned segment provides for a portion of the hose to be maintained in tension, at a distance away from the user at all times, thereby preventing entanglement while exerting an insignificant force on the mask.

The pre-determined tension is selected as the minimum tension required to support the tensioned segment of the hose away from the user. This effectively results in only an insignificant force being placed on the mask and minimizing the risk of the mask being pulled off by the hose support 100. In use, the tape 150 extends and retracts in response to movement of the user, thereby maintaining the tensioned segment away from the user.

Preferably, the pre-determined tension is user adjustable by operation of a tension adjustment mechanism. This allows the hose support 100 to be adapted for use with different types of CPAP, or oxygen machines and hoses, and thus forms an adjustable tension hose support 100. The user will set the pre-determined tension to a level which does not impart a noticeable force on the mask, while still sufficient for maintaining tension in the tensioned segment and keeping the tensioned segment of the hose away from the user. The structure and operation of the tension adjustment mechanism will be described in further detail below.

Figure 2:
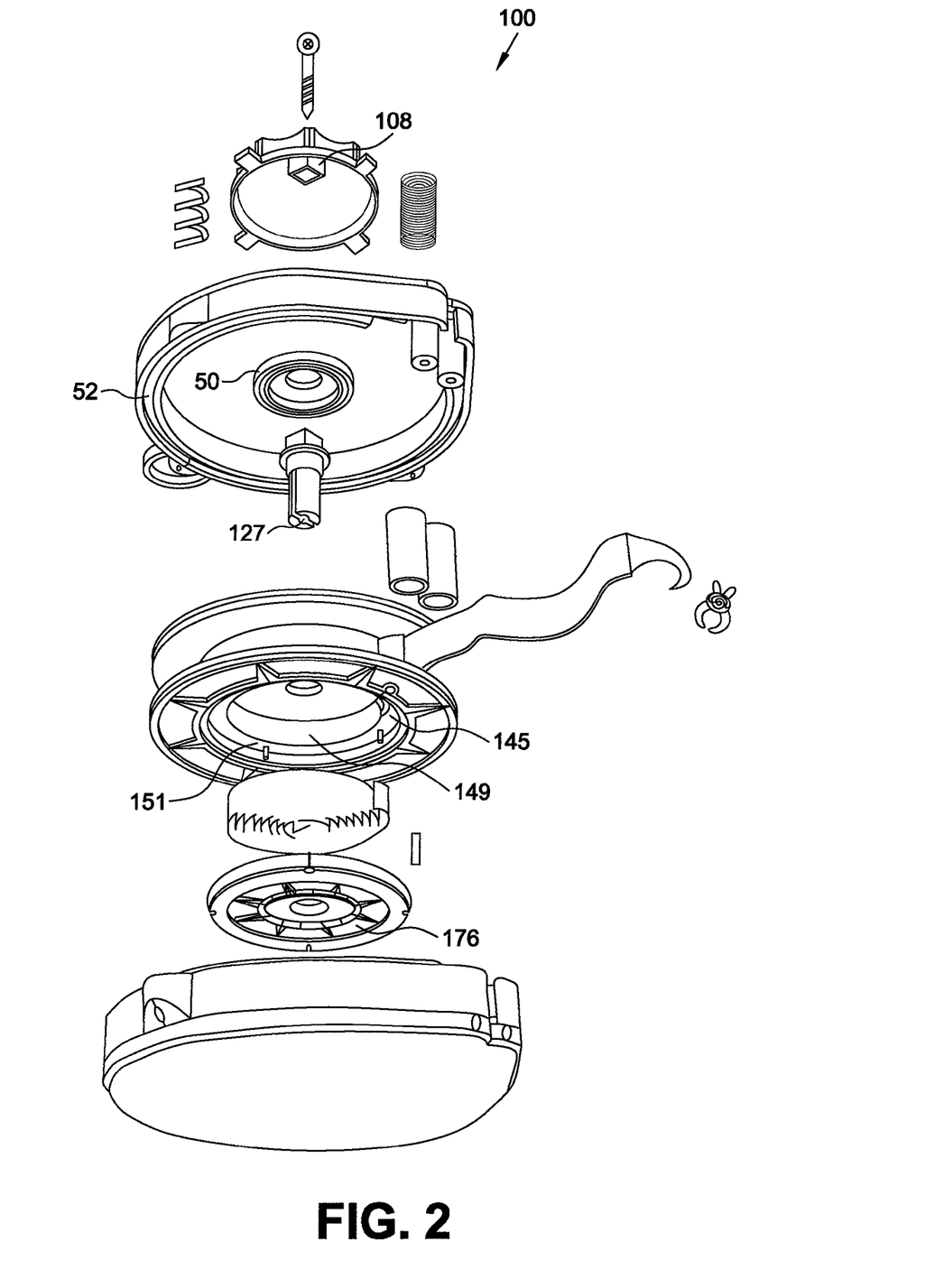
FIG. 2 is an exploded perspective view taken from the bottom of the hose support of FIG. 1.

In the illustrated embodiment, and referring particularly to FIGS. 1 and 2, housing portions 40 and 60 are shown to have a substantially corresponding shape and structural features which interact allowing for a close fitting relationship between the portions 40 and 60. Optionally, such close fitting relationship may be provided by an interacting male groove 64 and a female groove 52. Once the hose support 100 is assembled, the two portions 40 and 60 can be secured by screws, clips, bounding material or any other means. Furthermore, FIGS. 1 and 2 show male grooves 50 and 68 to support female groove 143 on reel 135, and female groove 176 on cover 170. The corresponding male grooves 50 and 68 and female grooves 143 and 176 allow the reel 135 to rotate freely in the housing 90, after securing the closure 170 onto seat 151.

Preferably, the reel 135 has a receptacle 149 for receiving the constant force spring 165 therein and a holder 145 for connecting one end of the constant force spring 165 within reel receptacle 149. An operative connection is provided between the tape 150 and the constant force spring 165 through reel 135 to maintain the tension in the tape 150. Such operative connection may be provided, for example, by a slit proximate one end of the constant force spring 165 sized and dimensioned to connect to holder 145 in reel receptacle 149 in a fixed manner. Closure 170 is shown to enclose the constant force spring 165 in the reel receptacle 149, and is positioned on the seat 151, and secured thereto by, for example, pins or a clip. The extendable end of constant force spring 165 is operatively connected to rotatable post 115. The rotatable post 115 has a split opening 123 for connecting the extendable end of constant force spring 165 therein. The post 115 passes through a reel opening 137 and a closure opening 174. The post 115 is preferably selectively rotatable. The rotatable post 115 is operatively connected to knob 102 to apply an initial tension to the constant force spring 165, thus allowing for the user to set the predetermined tension.

The post 115 comprises integrated element 119, gear 121 and ring 125. The element 119 and the gear 121 extend through opening 42, outside of the housing portion 40. The ring 125 supports the post 115, keeping it within housing portion 40. Thereon, the post 115 is operatively connected to a knob 102, shown in FIGS. 1 and 2, for applying a rotation to the post 115, and thus applying an initial tension to the constant force spring 165. The housing portion 60 optionally comprises a support, in the form of an axis pin 66 and a male groove 72, shaped to provide support for the split 123 and opening 127 at the other end of post 115. The aforementioned features are one example of how the post 115 can be supported, but other means for supporting the post 115 and otherwise providing an initial adjustable tension to the constant force spring 165 are within the scope of the present invention. Support pin 160 is optionally provided to connect one end of tape 150 through opening 139 of reel 135 to ensure the tape 150 is wound flush with the core 141 of the reel 135.

At the exterior of the housing 90, where the tape 150 passes through, a pair of rollers 110 is mounted around an opening 44. The rollers 110 are mounted on two posts 46. The rollers 110 allow for smooth movement of the tape 150 and act to reduce the friction and wear upon the housing 90 caused by the movement of the tape 150 through the opening 44. Furthermore, the rollers 110 prevent the tape 150 from twisting or jamming and reduce the friction and wear upon the tape 150 as it extends and retracts through the rollers 110. Positioned on the exterior of housing portion 40, preferably in knob receptacle 108, is one of a coil spring 112 or a silicone tube 111, in combination with two or more angle stoppers 48. The user pushes in knob 102 to disengage extensions 106 from angle stoppers 48, and subsequently rotates the knob 102 to increase or decrease the tension in the constant force spring 165. According to this embodiment the knob 102 is preferably mounted onto element 119 through the knob receptacle 108 and secured thereto by a screw 101 extending through opening 104 of knob 102, and one of coil spring 112 and silicone tube 111, and into threaded opening 117. The unthreaded portion 103 of screw 101, in combination with a gap between the end of element 119 and the far end of knob receptacle 108 allows knob 102 to be pushed down, thereby allowing the user to increase or decrease the tension in the constant force spring 165. Re-engaging extensions 106 and angle stopper 48 by holding the knob 102 in place, maintains the rotational position of knob 102 and the initial tension in the constant force spring 165. The coil spring 111 or silicone tube 112 provides resistance against the uncontrolled falling of knob 102.

While the hose support 100 may be designed for a specific hose and CPAP machine, such that the tension in the constant force spring 165 is fixed for a given hose, the tension is preferably adjustable such that prior to use, the user adjusts the tension to a minimum level where the hose is always supported away from the user, thereby preventing entanglement, and exerting a negligible force on the mask thus substantially eliminating the risk of the mask detaching from the user during sleep. Effectively, the tension in the spring 165 produces a pre-determined tension in the tape 150 that is the minimum required to maintain the tensioned portion of the hose in tension and overcome the force of gravity to hold the tensioned portion at some level away from the user, thus allowing the user to wear the mask comfortably fitted to their face.

While any mechanism may be used that adjusts the initial tension in the constant force spring 165, a few possible embodiments of the tension adjustment mechanism will now be described. These are for example only and are not intended to limit the invention.

Figure 3:
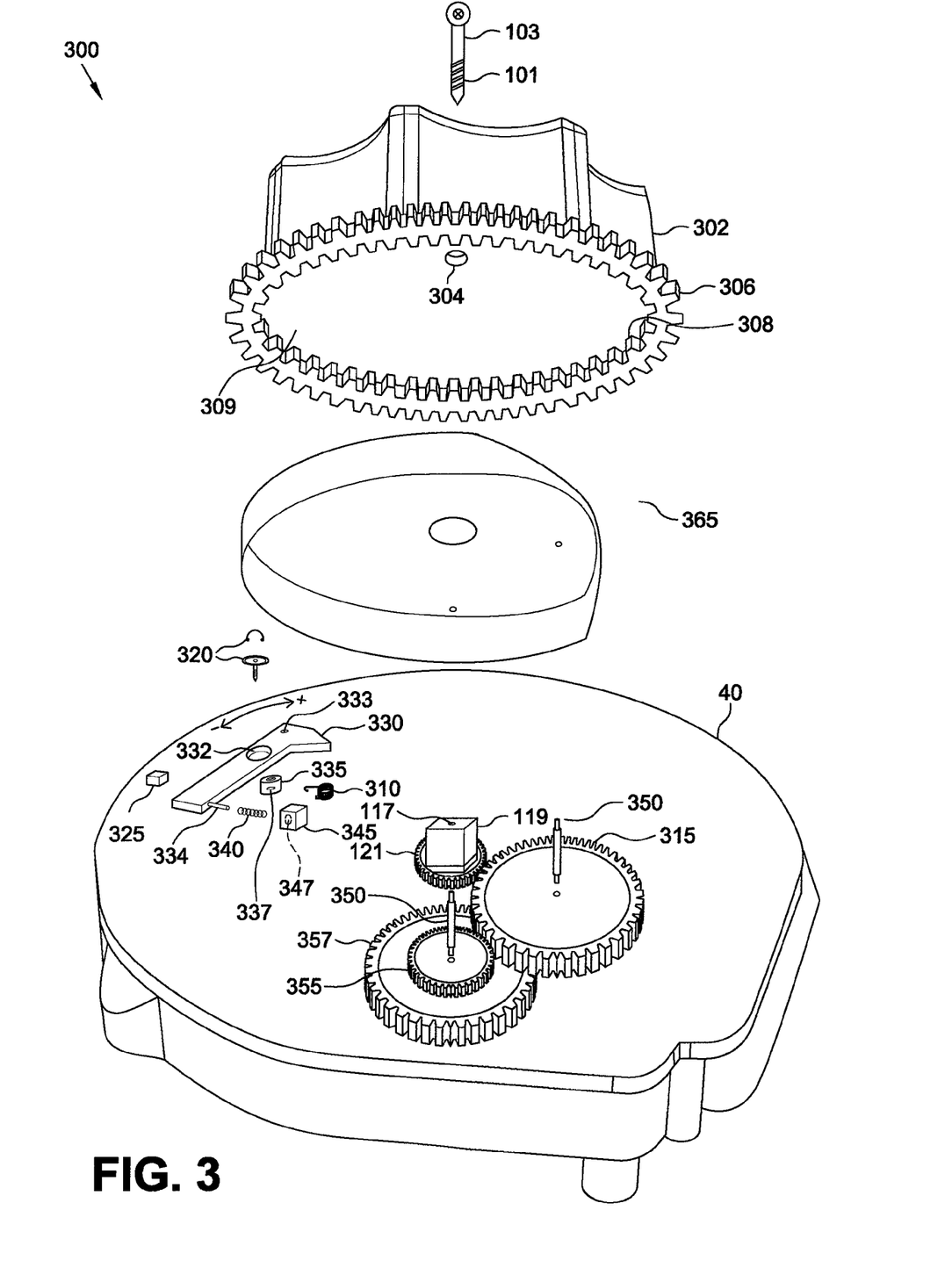
FIG. 3 is a perspective view of a tension adjustment mechanism according to a second embodiment, for use with hose support of the present invention.

Referring now to FIG. 3, there is shown a second embodiment of the tension adjustment mechanism 300 having a knob 302 with integrated gears 306 and 308. The gear 308 operatively engages post gear 121 via a series of gears 315, and integrated gears 355 and 357. The combination of gears allows for a gear reduction as desired such that a single turn of the knob 302 can result in a number of turns of the rotatable post 115. As such, slight rotations of knob 302 are required to set the initial tension in the constant force spring 165 (shown in FIG. 1). The knob 302 further includes an indented portion 309 to enclose the gears 315, 355, 357, 121, and element 119 upon cover 365. The gears 315 and integrated gears 355 and 357 are supported by pins 350 extending vertically from the housing portion 40 to cover 365, and supported by indents in housing portion 40 and cover 365. The cover 365 is secured, for example by screws, clips, bounding material or any other means known to one skilled in the art. Furthermore, indented portion 309 of knob 302 will house the cover 365 which knob 302 will be sitting and rotating. An operating manual for adjusting the tension of the hose support 100 may include optimal tension levels for common CPAP machines and hose combinations such that minimal experimentation is required by the user.

FIG. 3 also shows the exterior of housing portion 40, with an integrated circular threaded detent 335, detent 325 and bracket 345, on which a stopper 330 is mounted, and supported thereon at a given height, preferably determined by a spacer, and onto circular threaded detent 335 thereto by a screw, or clip 320, through opening 332 of stopper 330, and is supported by detent 325, and bracket 345. Bracket 345 has an indent 347 housing a coil spring 340 with a stopper pin 334 supporting the coil spring 340 to produce a force on stopper 330. Alternatively, a torsion spring 310 may be provided which hooks, on one side, into opening 337 of the circular threaded detent 335, and on the other side to opening 333 of stopper 330. In an in-use position, the stopper 330 engages the gear 306 to prevent rotation of the knob 302. Screw 101 includes an unthreaded portion 103 to connect the knob 302 to the post 115 via opening 367 of the cover 365, and into threaded opening 117, while allowing the knob 302 to rotate freely about the unthreaded portion 103. In order to rotate knob 302, and thereby decrease the tension in the coil spring 165 (shown in FIG. 1), the knob 302 is held while, depressing the stopper 330 against the force of coil spring 340, or torsion spring 310, thereby disengaging the gear 306, and allowing counterclockwise rotation of the knob 302. In use, the embodiment of FIG. 3 can be adapted such that clockwise rotation of the knob 302 increases the tension in the constant force spring 165 without depressing the stopper 330.

While the preferred tension adjustment mechanism has been described with respect to FIG. 3, it will be understood by those skilled in the art that other ways of adjusting the tension of the constant force spring 165 (FIG. 1), to allow for variance in the type of CPAP machine, and positioning of the adjustable tension hose support 100 are within the scope of the present invention. Some examples of preferred alternate tension adjustment mechanisms are now described below, and with reference to elements common to the embodiment of FIG. 3.

Figure 4:
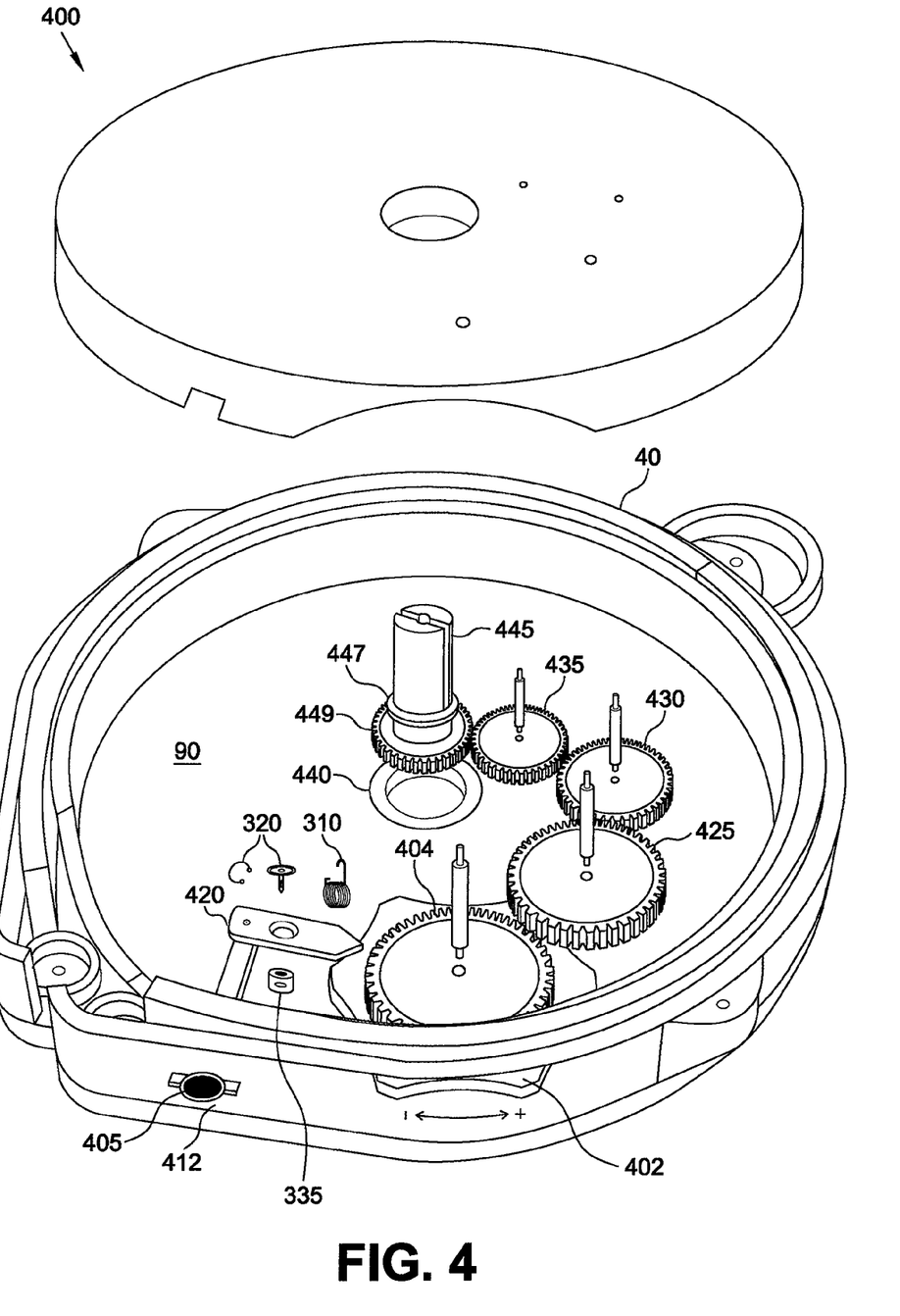
FIG. 4 is a perspective view of a tension adjustment mechanism according to a third embodiment, for use with hose support of the present invention.

FIG. 4 shows a third embodiment of the tension adjustment mechanism 400 mounted within housing 90, and preferably onto housing portion 40. As shown, the knob portion 405 of the lever stopper 412, and knob 402 partially extend outside of housing 90. The knob 402 has an integrated gear 404 that operatively engages a post gear 449 via a series of gears, for example, gears 425-430 and 435. The gear arrangement shown in FIG. 4 is for example only. It will be understood by those skilled in the art that any number of gears may be used, and arranged in any manner which allows for the results described below.

A single turn of the knob 402 can result in a number of turns of the rotatable post 445. The lever stopper 412 is supported on circular threaded detent 335, in a biased relationship, and secured as such by torsion spring 310, and a clip or screw 320. The gears 404, 425, 430 and 435 are supported by a cover and pins as was described above with respect to FIG. 3, and as such, will not be further described here. The rotatable post 445 preferably has an integrated male groove 447 for supporting female groove 143 of the reel 135, as shown in FIG. 1. The post 445 rotates freely within groove 440. The stopper 420 engages gear 404 and thus maintains the pre-determined tension in the constant force spring 165. In the preferred embodiment, and by way of example only, by holding the knob 402 and pulling on knob 405 of the lever stopper 412, then rotating the knob 402 clockwise decreases the tension in the constant force spring 165. Similarly, rotating knob 402 counterclockwise, without pulling on the knob 405 of the level stopper 412 increases the tension in the constant force spring 165. The "−" and "+" marks shown may be provided to indicate a direction of rotation to increase or decrease the tension in the constant force spring 165.

Figure 5:
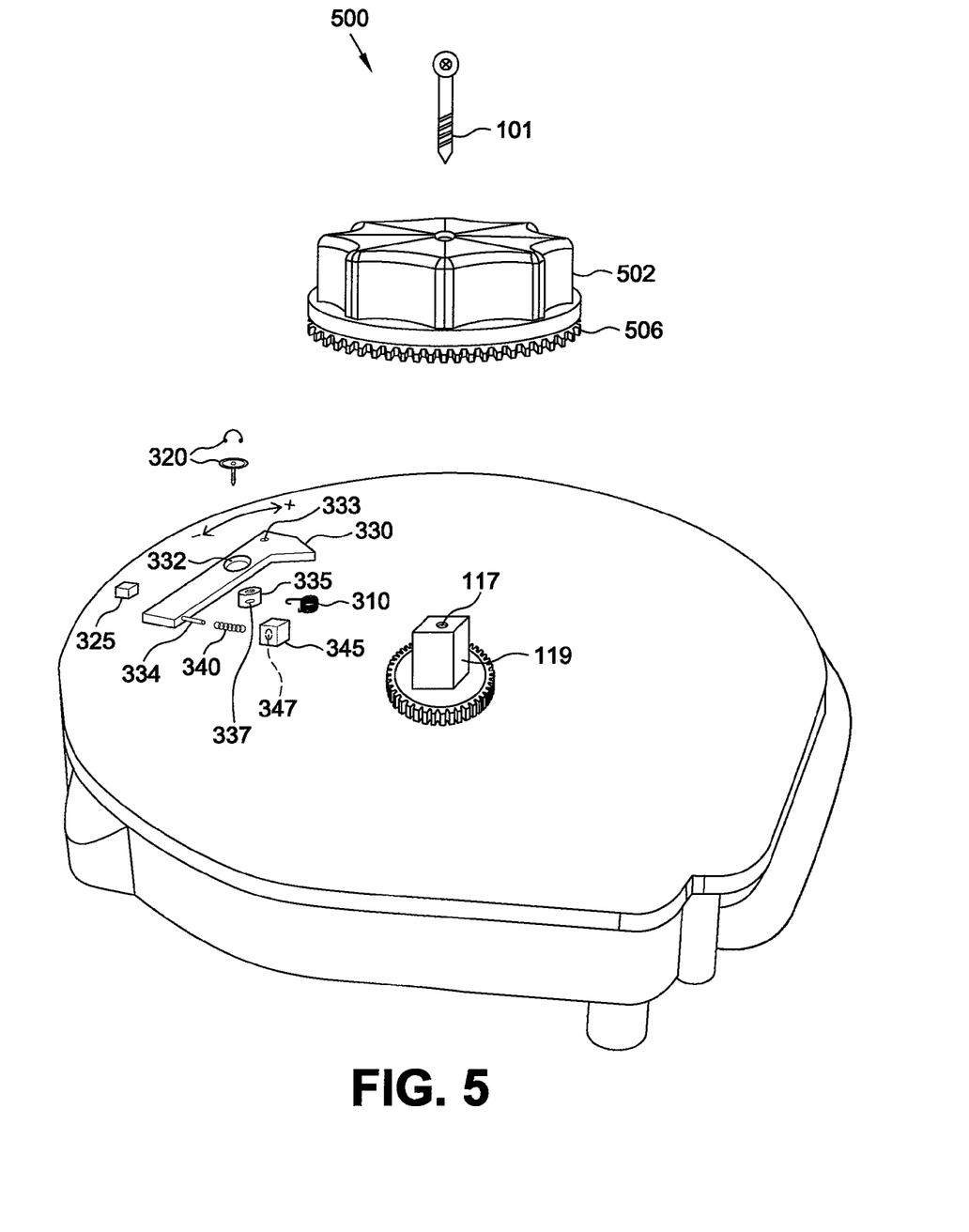
FIGS. 5 and 6 are exploded perspective views of alternate tension adjustment mechanisms for use with the hose support of the present invention.

FIG. 5 shows tension adjustment mechanism 500 with correspondingly numbered elements as in FIGS. 3 and 4, but including only one gear 506, for interaction with the stopper 330. As such, a higher number of turns of the knob 502 are required to produce a desired increase in the initial tension of the constant force spring 165 (FIG. 1). According to the embodiment of FIG. 5, the knob 502 is mounted directly unto element 119 through knob receptacle 504, and secured thereto by screw 101 extending through an opening at the top of knob 502 (not shown) and into threaded opening 117. Alternatively, a torsion spring 310 could be adapted to replace the bracket 345, the coil spring 340 and the stopper pin 334 shown in FIG. 3.

Figure 6:
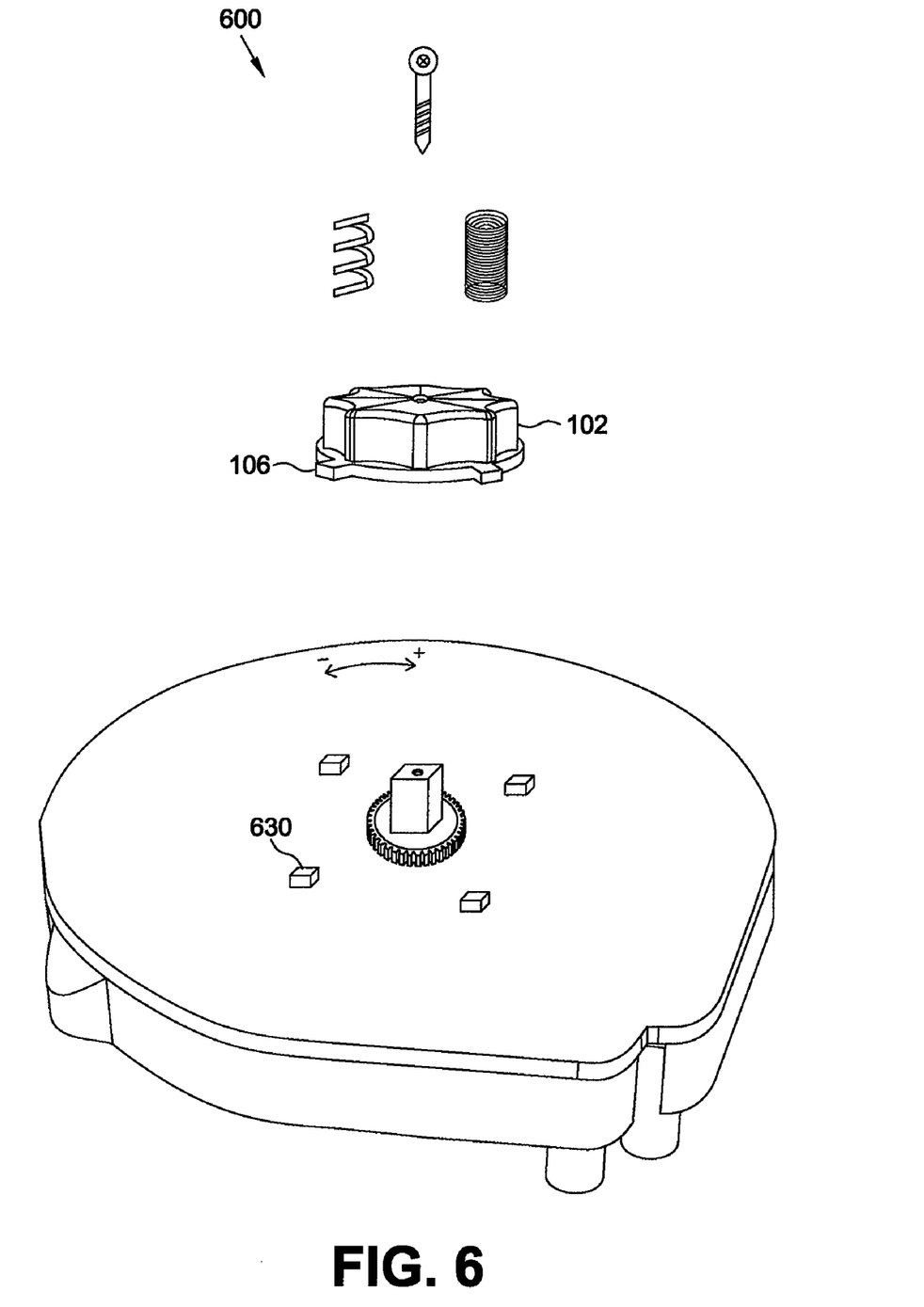

Referring now to FIG. 6, tension adjustment mechanism 600 is shown, having correspondingly numbered elements as FIG. 1, and having two or more detents 630. The user must pull out knob 102 to disengage extensions 106 from detents 630, and subsequently rotate the knob 102 to increase or decrease the tension in the constant force spring 165. Similarly numbered elements are not further described as they function substantially as described with respect to FIG. 1 above.

Preferably, the housing 90 is mounted at a level higher than that of the patient. This will ensure that the tensioned portion of the hose is sustained at a given height away from the user. This further prevents entanglement and also significantly reduces the likelihood that the hose will interfere with the user's sleep by coming into contact with the user and substantially eliminate pulling the mask away from the user. The preferred mounting means, and related elements, are shown in FIGS. 7-14, and are presented by way of example only. Other mounting means, as well as other elements used within the preferred mounting means, as would be appreciated by those skilled in the art, are contemplated by the present invention.

Figure 7:
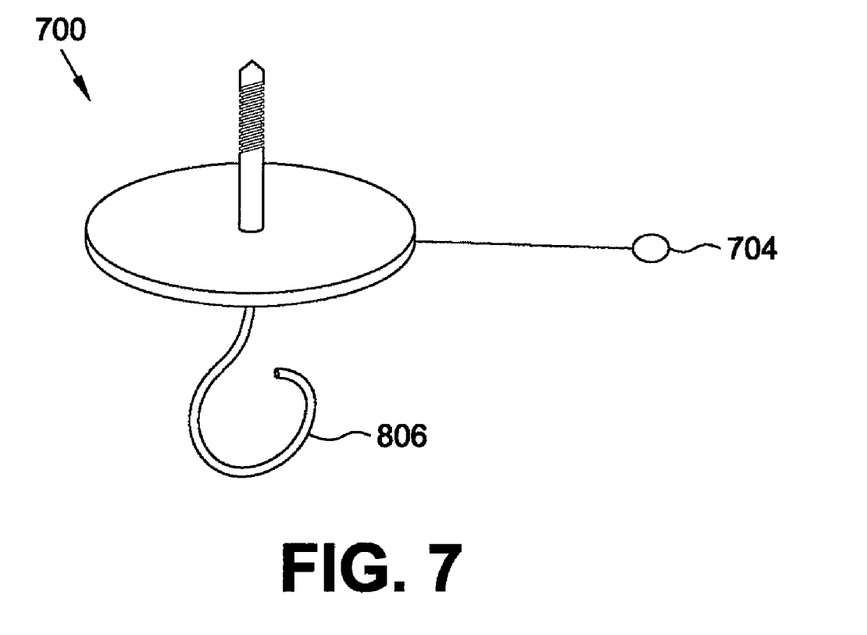
FIG. 7 is a schematic view of a ceiling mount for use with the hose support of FIG. 1.

In FIG. 7, a ceiling mount 700 is shown having a hook 706 for supporting the hose support 100. Drywall plugs, concrete plugs or screws, can be provided depending on the type of ceiling unto which the hook is attached. The safety cable 704 which is shown attached to the hook 700 may be used to secure the hose support 100 against accidental detachment from the ceiling.

Figure 8:
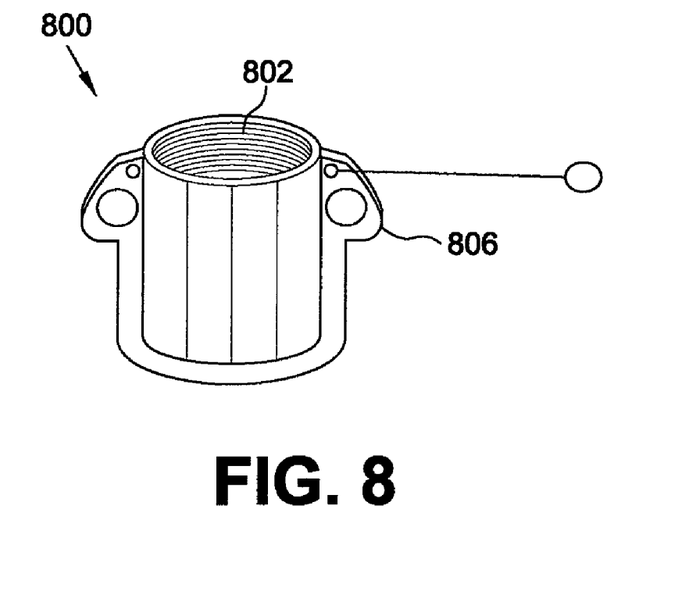
FIG. 8 is a schematic view of a wall mount for use with the hose support of FIG. 1.

FIG. 8 shows a wall mount bracket 800 having a threaded base 802 for receiving the threaded part portion 1412 of extended arm 1400 (shown in FIG. 14) therein. The extended arm 1400 has a hook 1414 on the one end for mounting the hose support 100. Where appropriate, drywall plugs or concrete plugs may be provided for receiving the appropriate mounting hardware, such as screws, to mount the bracket 800, through holes 806, and onto a wall. A safety cable may be provided as previously described with respect to FIG. 7.

Figure 9:
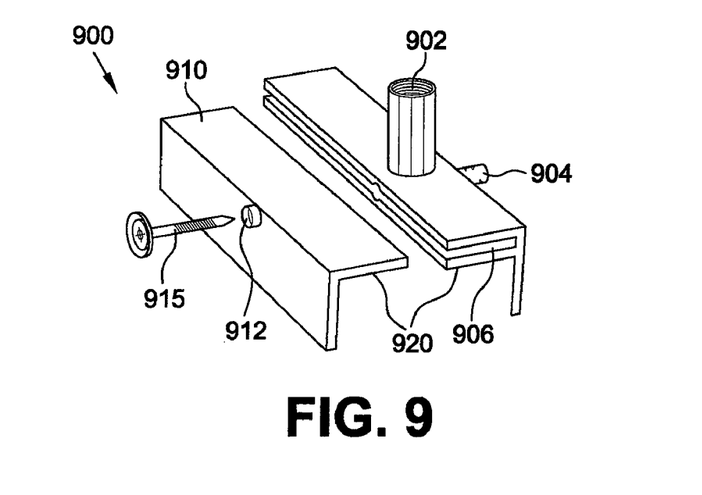
FIG. 9 is a schematic view of a head board mount for use with the hose support of FIG. 1.

FIG. 9 shows head board mount 900 including male 910 and female 906 vice portions, preferably coated on a headboard contacting side 920 with a protective grip material, such as silicone or rubber. The vice portions 906 and 910 are fastened to a headboard (not shown) with screw 915 passing through opening 912 into threaded opening 904. Female vice portion 906 has a threaded base 902 to receive and support the threaded portion 1310 at one of poles 1300 (shown in FIG. 13). At the top end of poles 1300, extended arm 1400 is mounted for supporting the adjustable tension hose support 100 in a manner similar to that of bracket 800. All mounting elements herein described may be manufactured in different sizes to fit various sizes of headboards.

Figure 10:
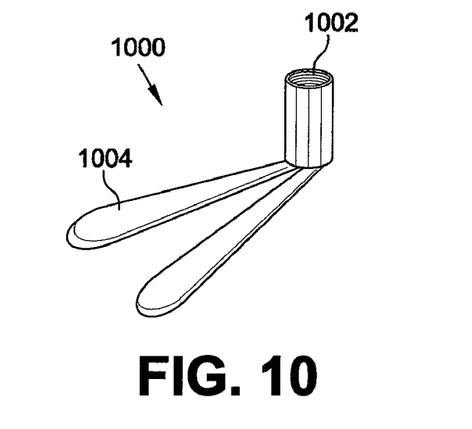
FIG. 10 is a schematic view of a mattress mount for use with the hose support of FIG. 1.

FIG. 10 shows an under-mattress mount 1000 having extensions 1004 extending underneath a mattress (not shown). The extensions 1004 are of a length such that the weight of the mattress over the length of the extensions 1004 is sufficient to support one of the poles 1300 shown in FIG. 13, in threaded base 1002. A portion of the pole 1300, proximate the mattress or other elements of the bed, is surrounded by a protective casing manufactured from a fabric or a rubber material. One of poles 1300 supports extended arm 1400 and hook 1414 (shown in FIG. 14) through threaded base 1305 to support the hose support 100, as previously described.

Figure 11:
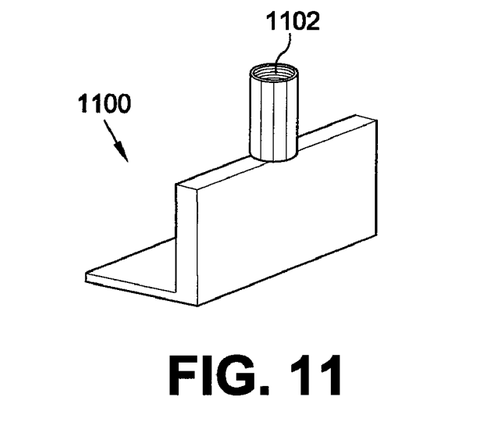
FIG. 11 is a schematic view of a bed frame mount for use with the hose support of FIG. 1.

FIG. 11 shows a bed frame mount 1100, similar to the mount shown in FIG. 10, but shaped and dimensioned to be supported between a bed frame and a box spring, and having threaded base 1102 to support one of poles 1300, with the extended arm 1400, therein, and thereby provide support for the hose support 100.

Figure 12:
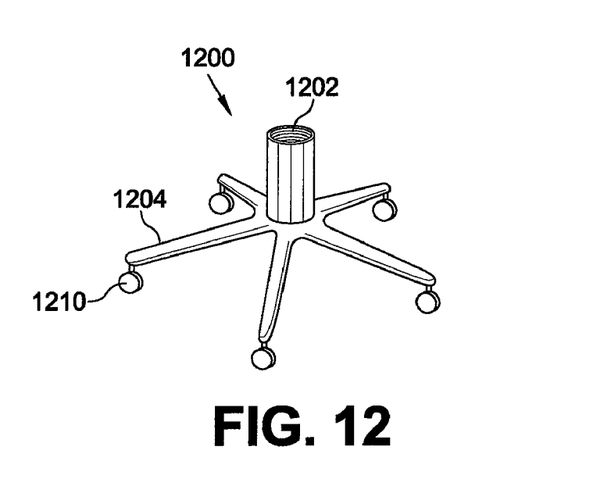
FIG. 12 is a schematic view of a floor mount for use with the hose support of FIG. 1.

FIG. 12 shows a floor mount 1200 with extensions 1204 supported on rollers 1210 for providing a transportable adjustable tension hose support 100. One of poles 1300 (shown in FIG. 13) extends upwardly from a threaded base 1202 and supports the extended arm 1400 extending therefrom, such that the adjustable tension hose support 100 may be attached to hook 1414 (shown in FIG. 14).

Figure 13:
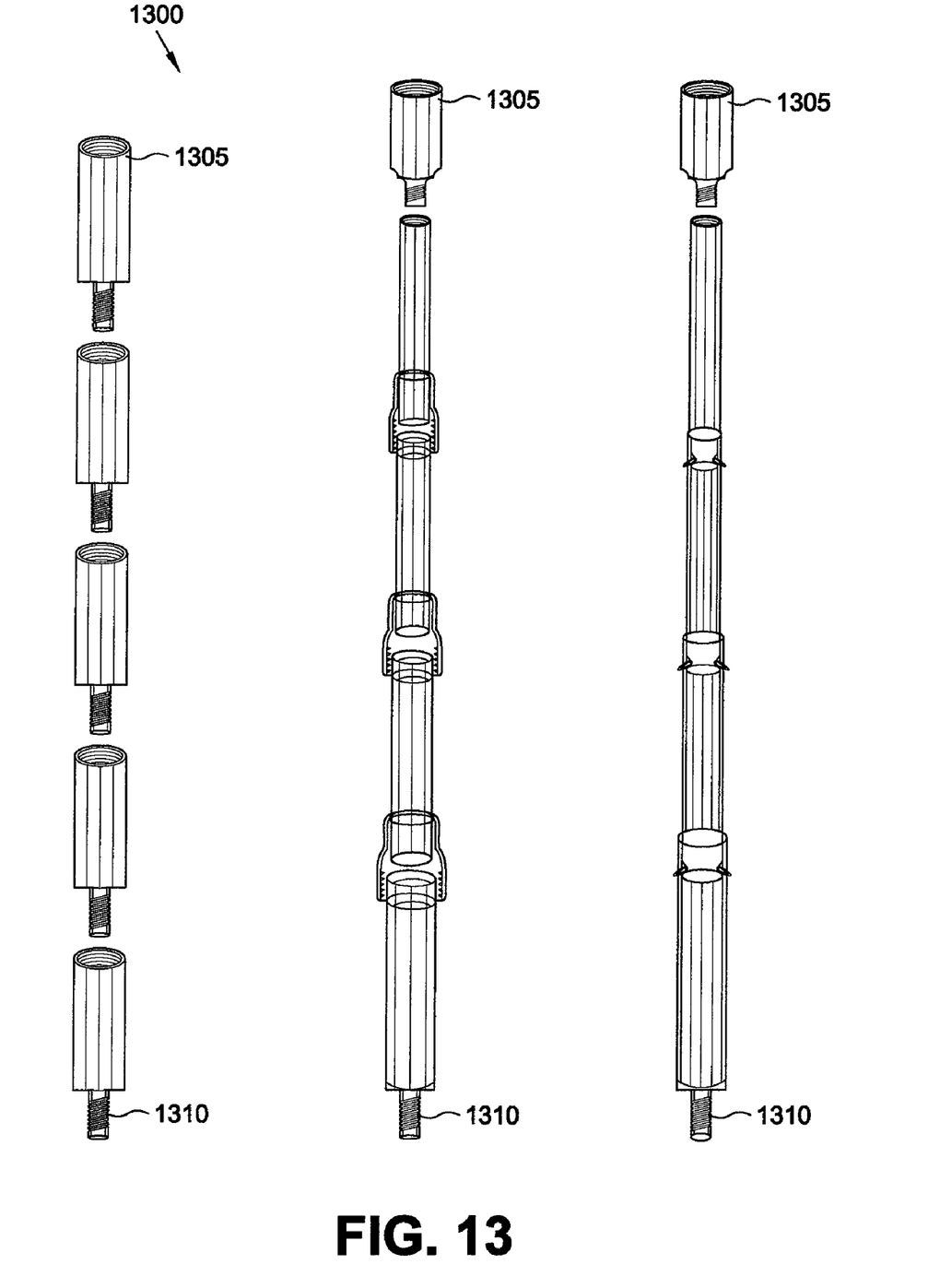
FIG. 13 is a schematic view of variable length poles for use in mounting the hose support of FIG. 1; and, FIG. 14 is a schematic view of an extended arm hook for use with the hose support of FIG. 1.
Figure 14:
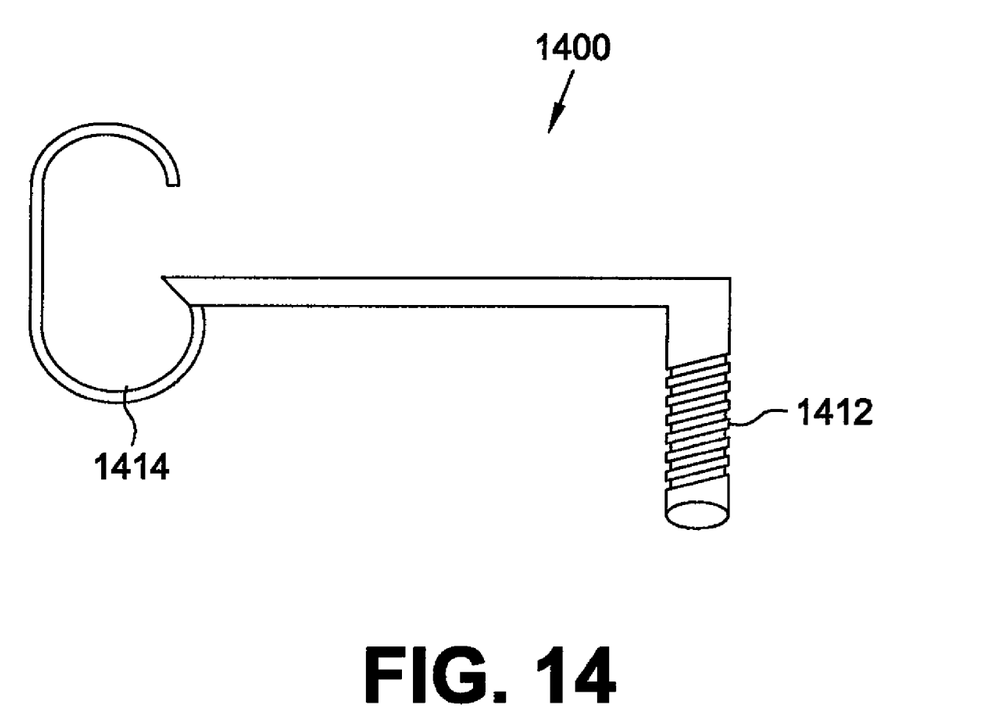

FIG. 13 shows examples of collapsible and telescoping poles 1300 as used in various embodiments of the present invention. The threaded parts 1310 are shown to be mounted into one of the threaded base of headboard mount 902, mattress mount 1002, bed frame mount 1102, or floor mount 1202 (shown in FIGS. 9-12). It will be apparent to one skilled in the art that other such poles or mounting means are within the scope of the present invention. FIG. 14 shows an extended arm 1400 with threaded part 1412 to mount into bracket 800 through threaded base 802, or unto one of poles 1300 through respective threaded base 1305.

While the above has been presented in the context of CPAP machines the support and method are equally applicable to any breathing hose and mask combination.

This concludes the description of several embodiments of the invention. The foregoing description has been presented for the purpose of illustration and is not intended to be exhaustive or to limit the invention to the precise form disclosed. It is intended the scope of the invention be limited not by this description but by the claims that follow.

What is claimed is:

1. A hose support for supporting a hose extending from a CPAP machine to a mask on a user, said hose support comprising:
    a housing,
    a reel mounted within said housing and having a tape wound thereon,
    a tensioning mechanism operatively connected to said tape for maintaining a pre-determined tension in said tape, such that the tape extends when under a tension greater than said pre-determined tension and retracts when slack is provided,
    a connector attached to a free end of said tape, said connector sized and dimensioned to be secured to a fixed position on the hose; said fixed position defining a tensioned segment of the hose, extending from said connector to the mask,
    a tension adjusting mechanism for adjusting said pre-determined tension,
    wherein said pre-determined tension is selected to support the tensioned segment of the hose away from the user, and wherein said tape extends and retracts in response to movement of the user, thereby maintaining the tensioned segment away from the user.

2. A hose support according to claim 1, wherein said tensioning mechanism comprises a constant force spring having a fixed end operatively connected within said reel.

3. A hose support according to claim 1, wherein said tension adjusting mechanism comprises a selectively rotatable post connected to an extendable end of said constant force spring for applying an initial tension to said constant force spring.

4. A hose support according to claim 3, wherein said selectively rotatable post is operatively connected to a knob on an exterior of said housing.

5. A hose support according to claim 3, wherein said selectively rotatable post is operatively connected to a knob on the interior of said housing.

6. A hose support according to claim 4, further comprising one or more reduction gears engaging said knob and said selectively rotatable post.

7. A hose support according to claim 5, further comprising one or more reduction gears engaging said knob and said selectively rotatable post.

8. A hose support according to claim 4, wherein said knob engages one or more stoppers on said housing to maintain the predetermined tension in said tape by maintaining the position of said knob.

9. A hose support according to claim 5, wherein said knob engages one or more stoppers on said housing to maintain the predetermined tension in said tape by maintaining the position of said knob.

10. A hose support according to claim 1, further comprising two or more rollers positioned at an exit of said housing to orient said tape with respect to said reel.

11. A hose support according to claim 1, further comprising a mounting device for mounting said housing at a position higher than the user.

12. A hose support according to claim 11, wherein said mounting device is adapted for mounting on a wall or a ceiling.

13. A hose support according to claim 11, wherein said mounting device comprises a base attached to any one of a head board mount, a mattress mount, a bed frame mount and a floor mount, and a pole extending therefrom for positioning said mounting device at said position higher than the user.

14. A hose support according to claim 1, comprising a base having a pole extending therefrom and having an arm extending from said pole for supporting said housing at a position higher than the user.

15. A hose support according to claim 13, wherein said base and said pole are collapsible into a size and dimension similar to the CPAP machine for storage and transport.

16. A hose support according to claim 14, wherein said base and said pole are collapsible into a size and dimension similar to the CPAP machine for storage and transport.

* * * * *